United States Patent [19]

Lee

[11] 4,374,295

[45] Feb. 15, 1983

[54] CATALYTIC CONVERSION OF METHANOL TO LIGHT OLEFINS

[75] Inventor: Carol S. Lee, Princeton, N.J.

[73] Assignee: Mobil Oil Corporation, New York, N.Y.

[21] Appl. No.: 368,496

[22] Filed: Apr. 15, 1982

[51] Int. Cl.³ .................... C07C 1/20; C07C 1/253
[52] U.S. Cl. .................................................. 585/640
[58] Field of Search ............................. 585/640, 638

[56] References Cited

U.S. PATENT DOCUMENTS

| | | | |
|---|---|---|---|
| 3,894,107 | 7/1975 | Butter et al. | 585/640 |
| 3,911,041 | 10/1975 | Kaeding et al. | 260/682 |
| 3,979,472 | 9/1976 | Butter | 260/668 R |
| 4,025,575 | 5/1977 | Chang et al. | 585/640 |
| 4,025,576 | 5/1977 | Chang et al. | 585/640 |
| 4,049,573 | 9/1977 | Kaeding | 252/432 |
| 4,049,735 | 9/1977 | Chen et al. | 585/640 |
| 4,066,714 | 1/1978 | Rodewald | 260/682 |
| 4,083,889 | 4/1978 | Caesar et al. | 585/640 |
| 4,100,219 | 7/1978 | Rodewald | 260/682 |
| 4,278,565 | 7/1981 | Chen et al. | 585/640 |

FOREIGN PATENT DOCUMENTS

| | | | |
|---|---|---|---|
| 6501 | 1/1980 | European Pat. Off. | 585/640 |
| 2061999A | 5/1981 | United Kingdom | 585/640 |

Primary Examiner—Delbert E. Gantz
Assistant Examiner—Cynthia A. Prezlock
Attorney, Agent, or Firm—Charles A. Huggett; Michael G. Gilman; George W. Allen

[57] ABSTRACT

A process for converting a methanol feed to light olefins over a zeolite catalyst comprising at least some crystalline aluminosilicate zeolitic material having a Constraint Index of about 1 to 12 and a silica/alumina mole ratio of at least about 12, e.g., ZSM-5, in the presence of an aldehyde-containing diluent comprising formaldehyde, acetaldehyde or mixtures thereof, under methanol conversion conditions. By using such a ZSM-5 type zeolite catalyst and an aldehyde-containing diluent, methanol can be converted to an olefin-containing hydrocarbon product enriched in $C_2$ to $C_4$ olefins such as ethylene.

8 Claims, No Drawings

CATALYTIC CONVERSION OF METHANOL TO LIGHT OLEFINS

BACKGROUND OF THE INVENTION

1. Field of the Invention

This invention relates to an improved process for converting a methanol feed to light olefins over crystalline aluminosilicate zeolite catalysts.

2. Description of the Prior Art

A remarkable growth in the production of synthetic fibers, plastics and rubber has taken place in recent decades. Such growth, to a large extent, has been supported and encouraged by an expanding supply of inexpensive petroleum raw materials such as ethylene and propylene. However, increasing demand for these light olefins has, from time to time, led to periods of shortage, either due to a diminished supply of suitable feedstocks or to limited processing capacity. In any event, it is now considered highly desirable to provide efficient means for converting raw materials other than petroleum to light olefins.

One such non-petroleum source of light olefins is coal-derived methanol. In this respect, it is known that methanol can be catalytically converted to olefin-containing hydrocarbon mixtures by contact under certain conditions with particular types of crystalline zeolite catalyst materials. U.S. Pat. No. 4,025,575, issued May 24, 1977, to Chang et al. and U.S. Pat. No. 4,083,889, issued Apr. 11, 1978 to Caesar et al., for example, both disclose processes whereby methanol and/or methyl ether can be converted to an olefin-containing product over a ZSM-5 type (Constraint Index 1–12) zeolite catalyst. ZSM-5, in fact, converts methanol and/or methyl ether to hydrocarbons containing a relatively high concentration of light ($C_2$ and $C_3$) olefins.

It is known that such light olefin production from the catalytic conversion of methanol can be optimized by varying one or more reaction parameters. Modification of the ZSM-5 type zeolite catalyst with, for example, silica, phosphorus, metal ions or metal oxides, can enhance selectivity of the methanol conversion reaction for production of light olefins. Likewise, utilization of dilute methanol feeds or inert diluents can also tend to increase selectivity of the reaction toward ethylene and light olefin production. Notwithstanding the existance of processes suitable for converting methanol to high yields of light olefins, there is a continuing need to develop additional catalytic procedures suitable for converting an organic charge comprising methanol to light olefin products with improved ethylene and light olefin selectivity.

Accordingly, it is an object of the present invention to provide an improved process for converting a methanol feed to olefin-containing products with high selectivity to production of light olefins.

It is a further object of the present invention to provide such a selective methanol conversion process which can be employed in conjunction with known catalysts and processes for maximizing light olefin production from methanol.

It is a further object of the present invention to provide such a selective methanol conversion process employing conventional catalysts, readily available reactants and diluents and commercially practical reaction conditions.

SUMMARY OF THE INVENTION

In accordance with the present invention, a process is provided for the selective conversion of a methanol feed to a hydrocarbon mixture rich in light olefins. The catalyst employed in such a process comprises at least some crystalline aluminosilicate zeolite material characterized by a Constraint Index of about 1 to 12 and a silica to alumina molar ratio of at least about 12, e.g. ZSM-5. Methanol conversion over such a catalyst occurs in a reaction zone under conversion conditions in the presence of aldehyde-containing diluent comprising formaldehyde, acetaldehyde or mixtures thereof. This aldehyde-containing diluent can be co-fed to the reaction zone in an amount sufficient to increase the selectivity of the conversion reaction to production of $C_2$–$C_4$ olefins.

DETAILED DESCRIPTION OF THE INVENTION

In accordance with the present invention, a methanol feed is catalytically converted to a hydrocarbon product rich in olefins. The term "methanol feed" as used herein designates only the organic material used as feed, i.e the organic compounds subjected to catalytic conversion to olefins, even though the total charge to the conversion reaction zone may contain additional components such as water. Since methanol is miscible with water, the charge to the catalytic reaction zone may actually contain large amounts of water, but only the methanol, and associated organic compounds, constitutes the methanol feed. Thus, all computable quantities referred to methanol feed, such as composition and weight hourly space velocity (WHSV), for purposes of the present invention are to be computed on a substantially anhydrous basis.

Any methanol product comprising at least 60 wt. % of methanol may be used to provide methanol for the methanol feed in this invention. Substantially pure methanol, such as industrial grade anhydrous methanol, is eminently suitable. Crude methanol, which usually contains from 12 to 20 wt. % water, or more dilute solutions, also may be used.

Small amounts of impurities such as higher alcohols or other oxygenated compounds in the methanol feed have little effect on the conversion reaction of this invention. The methanol feed may contain minor amounts of methyl ether. When this component is present, it is preferred that it constitute not more than about 20 wt. % of the total methanol feed. For purposes of the present invention, it is contemplated to directly convert methanol feed to the hydrocarbon mixture characterized by a high content of light olefins. Such amounts of methyl ether as may be formed concomitantly in the conversion reaction, however, may be recovered and recycled with fresh methanol feed, and the methyl ether content calculated on the total of recycle and fresh feed will not ordinarily exceed the above-noted 20 wt. %.

In one embodiment of the present invention, the charge to the reaction zone comprises only the methanol feed as hereinbefore described. In another preferred embodiment of the present process, selectivity of the methanol conversion reaction for production of light olefins can be increased by contacting methanol feed with the hereinafter described zeolite based catalyst in the presence of up to about 20 mols, and preferably from about 1 to 10 mols of steam per mol of methanol feed. Such steam contact is made in the reaction zone under the methanol conversion conditions hereinafter described. Such steam may be provided directly by injecting the requisite amount of water or steam into the reaction zone. Alternatively, steam may be provided totally or in part by water mixed with the methanol feed in a molar ratio of water to methanol feed of up to about 20:1, preferably from about 1:1 to 10:1. Such water in the charge to the reaction zone, of course, forms steam in the reaction zone under the conversion conditions of the present invention.

The methanol feed as hereinbefore described is catalytically converted to a light olefin enriched hydrocarbon product by contact with a catalyst comprising a particular type of crystalline aluminosilicate zeolite material which exhibits unusual properties. Although such zeolites have usually low alumina contents, i.e. high silica to alumina mole ratios, they are very active even when the silica to alumina mole ratio exceeds 30. Such activity is surprising, since catalytic activity is generally attributed to framework aluminum atoms and/or cations associated with these aluninum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this particular class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intracrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. 70 and above or even 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also to be included within this definition are substantially pure silica analogs of the useful zeolites described herein, that is to say those zeolites having no measurable amount of aluminum (silica to alumina mole ratio of infinity) but which otherwise embody the characteristics disclosed.

Members of this particular class of zeolites, after activation, acquire an intracrystalline sorption capacity for normal hexane which is greater than that for water, i.e. they exhibit "hydrophobic" properties. This hydrophobic character can be used to advantage in some applications.

The zeolites of the particular class useful herein have an effective pore size such as to freely sorb normal hexane. In addition, their structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of about 1 to 12. Constraint Index (CI) values for some typical materials are:

| Zeolite | C.I. |
|---|---|
| ZSM-5 | 8.3 |
| ZSM-11 | 8.7 |
| ZSM-12 | 2 |

-continued

| Zeolite | C.I. |
| --- | --- |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than a exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The particular class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 is more particularly described in European patent application No. 80 300,463 published Sept. 3, 1980 as Publication No. 0015132, the entire content of which is incorporated herein by reference.

It is to be understood that by incorporating by reference the foregoing patent documents to describe examples of specific members of the specified zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired.

Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article Zeolite Structure by W. M. Meier. This paper, the entire contents of which are incorporated herein by reference, is included in Proceedings of the Conference on Molecular Sieves, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used as precursors to the alkaline-earth metal modified zeolites of the present invention. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing methanol conversion processes using the catalysts of the present invention, it may be useful to incorporate the above-described crystalline zeolites with a matrix comprising another material resistant to the temperature and other conditions employed in such processes. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The zeolite composites as described may be further modified if desired to alter their catalytic properties with respect to their utility in promoting conversion of methanol to a hydrocarbon product. It is known, for example, to modify such zeolites by incorporating various materials into or onto such zeolite composites prior to their use for methanol conversion. For example, Rodewald; U.S. Pat. No. 4,100,219; Issued July 11, 1978 discloses zeolite-based methanol conversion catalysts treated with a silicone or silane material to incorporate amorphous silica with the zeolite. Rodewald; U.S. Pat. No. 4,066,714; Issued Jan. 3, 1978 discloses zeolite-based methanol conversion catalysts modified by incorporation of metal cations having an ionic radius exceeding 1 Angstrom, e.g. cesium and barium. Kaeding; U.S. Pat. No. 4,049,573; Issued Sept. 20, 1977 discloses zeolite-based methanol conversion catalysts modified by incorporation of oxides of boron or magnesium and/or phosphorus. Butter; U.S. Pat. No. 3,979,472; Issued Sept. 7, 1976 discloses zeolite-based methanol conversion catalysts modified by incorporation of antimony oxide. Kaeding et al.; U.S. Pat. No. 3,911,041; Issued Oct. 7, 1975 discloses zeolite-based methanol conversion catalysts modified by incorporation of oxides of phosphorus. All of the foregoing patents are incorporated herein by reference.

The process of the present invention involves utilization of the above-described catalyst compositions, whether modified or not, to promote the selective conversion of methanol feed to hydrocarbons, particularly light ($C_2$–$C_4$) olefins. The methanol feed as hereinbefore described can be contacted in the vapor phase with the particular catalyst materials, also hereinbefore described, in a reaction zone and under reaction conditions suitable for effecting conversion of the methanol feed to olefins. Such conversion conditions include an operating temperature between about 200° C. and 500° C., preferably 275° C. and 425° C., a pressure between about 5 psia (~35 kPa) and 500 psia (3447 kPa), preferably about 15 psia (103 l kPa) and 100 psia (689 kPa); and a weight hourly space velocity (WHSV) of the methanol feed of between about 0.05 and 30, preferably 0.1 and 10.

In accordance with the present invention, it has been discovered that especially desirable light olefin-selective methanol conversion results can be achieved by conducting the conversion reaction under the aforementioned reaction conditions and in the presence of an aldehyde-containing diluent comprising formaldehyde, acetaldehyde or mixtures thereof. The preferred aldehyde for use in or as the diluent is formaldehyde (HCHO). The diluent can thus comprise substantially pure formaldehyde gas or can comprise aqueous solutions of formaldehyde. Commercial grades of formaldehyde are quite acceptable including the 37%, 44% and 50% aqueous solutions known as formalin. Such formalin solutions generally also contain up to 15% methanol to inhibit formaldehyde polymerization.

The aldehyde-containing diluent can also comprise acetaldehyde, either as the sole aldehyde or in admixture with formaldehyde. Acetaldehyde ($CH_3CHO$) is generally available as technical grade 99% acetaldehyde.

Formaldehyde and/or acetaldehyde from any source can be admixed with inert liquid or gaseous materials to form the diluent co-fed to the reaction zone along with the methanol charge. Such inert materials include water, hydrogen, nitrogen, carbon dioxide, $C_1$ to $C_7$ hydrocarbons or flue gas.

The aldehyde-containing diluent may be admixed with the methanol feed or can be introduced separately into the reaction zone. It is also contemplated that aldehyde diluent can be provided at least in part by converting a fraction of the methanol feed to formaldehyde in the presence of a dehydrogenation or oxidation catalyst.

Such an aldehyde-containing diluent from whatever source can be fed to the reaction zone in an amount sufficient to increase the selectivity of the conversion reaction to the production of $C_2$ to $C_4$ olefins. Generally a molar ratio of aldehyde to methanol of about 0.001:1 to 0.1:1 can be employed. More preferably the aldehyde to methanol molar ratio varies from about 0.005:1 to 0.05:1. The diluent can be co-fed to the reaction zone using a weight hourly space velocity (WHSV) of from about 0.00025 to 1.5, preferably from about 0.001 to 0.1, based upon pure aldehyde.

The methanol conversion process described herein may be carried out as a batch-type, semi-continuous or continuous operation utilizing a fixed, fluidized or moving bed catalyst system. A preferred embodiment entails use of a catalyst zone wherein the alcohol charge together with aldehyde-containing diluent and optionally with added water is passed concurrently or countercurrently through a fluidized or moving bed of particle-form catalyst. The latter after use may be conducted to a regeneration zone wherein the aged catalyst can be regenerated by appropriate regeneration procedures. After regeneration, the regenerated catalyst can be recycled to the conversion zone for further contact with the methanol and/or ether containing feed.

The product stream in the process of the present invention contains steam and a hydrocarbon mixture of paraffins and olefins, substantially devoid of aromatics. This mixture is particularly rich in light olefins, i.e., ethylene, propylene, and butylene. Generally, a major fraction of the total olefins is ethylene plus propylene with the ethylene content of the product exceeding the propylene content. Thus, the predominant hydrocarbon product constitutes valuable petrochemicals. The steam and hydrocarbon products may be separated from one another by methods well known in the art. In a preferred embodiment of the invention, the unconverted methanol and/or methyl ether, as well as at least part of the water in the product, can be recycled to the reaction zone.

The following examples will serve to illustrate the process of this invention without limiting the same.

EXAMPLE I

Methanol feeds containing methanol/water mixtures in combination with various types of diluents are catalytically converted to hydrocarbon products over a ZSM-5 zeolite having a crystallite size of about 1 micron and a silica to alumina molar ratio of about 70:1. The zeolite is admixed with alumina binder to form a composite comprising 65% zeolite and 35% binder. In one instance, the zeolite is pretreated by contacting it with steam at 1000° C. for 7 hours.

About 1.5 grams of such a catalyst is placed in a reactor maintained at about 300° C. Various methanol-containing charges are fed to the reactor at 9.24 ml/hr. In some instances, an aldehyde diluent is also introduced. Temperature is adjusted within the 300°–375° C. range to obtain $CH_2$ conversion (methanol and methyl ether) values of about 50%. For 50% $CH_2$ conversion, selectivities to ethylene and $C_2$–$C_4$ olefins are determined by interpolation. Catalyst type, reactant descriptions, space velocities and selectivities to ethylene and $C_2$–$C_4$ olefins are set forth in Table I.

TABLE I

| Light Olefins from Methanol Over HZSM-5/$Al_2O_3$ | | | | |
|---|---|---|---|---|
| Catalyst | | WHSV | $C_2=$ (Wt %) | Total $C_2=-C_4=$ (Wt %) |
| A. HZSM-5 | MeOH | 3.1 | 27.7 | 53.6 |
| | $H_2O$ | 5.3 | | |
| B. HZSM-5 | MeOH | 3.1 | 31.1 | 59.5 |
| | $H_2O$ | 5.3 | | |
| | HCHO | 0.03 | | |
| C. Steamed HZSM-5 | MeOH | 1.15 | 30.0 | 63.1 |
| | $H_2O$ | 1.94 | | |
| | HCHO | 0.01 | | |
| D. HZSM-5 | MeOH | 3.1 | 30.2 | 58.7 |
| | $H_2O$ | 5.3 | | |
| | $CH_3CHO$ | 0.03 | | |

The Table I data indicate that selectivity of the methanol conversion reaction to both ethylene and total $C_2$–$C_4$ olefin production can be improved by co-feeding formaldehyde or acetaldehyde to the reaction zone.

What is claimed is:

1. In a process for producing a hydrocarbon mixture containing light olefins by contacting a methanol feed with a catalyst comprising a crystalline aluminosilicate zeolite having a Constraint Index of about 1 to 12 and a silica to alumina molar ratio of at least about 12, said contacting occurring in a reaction zone under methanol conversion reaction conditions, the improvement which comprises:

co-feeding to said reaction zone along with said methanol feed an aldehyde-containing diluent comprising formaldehyde, acetaldehyde or a mixture thereof, in an amount sufficient to increase the selectivity of the conversion reaction for production of $C_2$ to $C_4$ olefins.

2. A process according to claim 1 wherein the aldehyde component of said diluent is formaldehyde.

3. A process according to claim 1 wherein said zeolite is selected from ZSM-5, ZSM-11, ZSM-12, ZSM-23, ZSM-35, ZSM-38 and ZSM-48.

4. A process according to claim 3 wherein the methanol conversion reaction conditions include a temperature of from about 200° C. to 500° C., and a reaction zone pressure from about 5 psia to 500 psia.

5. A process according to claim 3 wherein the weight hourly space velocity of the aldehyde in said diluent ranges from about 0.00025 to 1.5 and the molar ratio of aldehyde to methanol ranges from about 0.001:1 to 0.1:1.

6. A process according to claim 5 wherein said diluent comprises mixtures of formaldehyde and water.

7. A process according to claim 6 wherein said methanol feed is admixed with water and with said diluent such that water is present in an amount of from about 1 mol to 10 mols of water per mole of methanol.

8. A process according to claim 1, 2, 3, 4, 5, 6 or 7 wherein said catalyst further comprises a binder for said zeolite material.

* * * * *